(12) United States Patent
Gerber et al.

(10) Patent No.: US 8,414,918 B2
(45) Date of Patent: *Apr. 9, 2013

(54) STABLE IMATINIB COMPOSITIONS

(75) Inventors: Bella Gerber, Petah-Tiqva (IL); Zvika Doani, Tel-Mond (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 895 days.

This patent is subject to a terminal disclaimer.

(21) Appl. No.: 12/238,328

(22) Filed: Sep. 25, 2008

(65) Prior Publication Data

US 2009/0092669 A1    Apr. 9, 2009

Related U.S. Application Data

(60) Provisional application No. 60/995,321, filed on Sep. 25, 2007, provisional application No. 60/995,651, filed on Sep. 26, 2007.

(51) Int. Cl.
*A61K 9/20* (2006.01)
*A61K 9/28* (2006.01)
*A61K 31/47* (2006.01)

(52) U.S. Cl. .................... 424/464; 424/474; 514/252.14

(58) Field of Classification Search ........................ None
See application file for complete search history.

(56) References Cited

U.S. PATENT DOCUMENTS

| | | | |
|---|---|---|---|
| 5,521,184 A | 5/1996 | Zimmerman | |
| 6,106,843 A * | 8/2000 | Muthukumarappa et al. ........................ | 424/261.1 |
| 6,894,051 B1 | 5/2005 | Zimmermann et al. | |
| 7,329,661 B2 | 2/2008 | Buerger et al. | |
| 7,977,348 B2 * | 7/2011 | Jegorov et al. ................ | 514/275 |
| 2004/0142864 A1 | 7/2004 | Bremer et al. | |
| 2004/0248918 A1 | 12/2004 | Kim et al. | |
| 2005/0209452 A1 | 9/2005 | Bornsen et al. | |
| 2005/0232990 A1 | 10/2005 | Boehm et al. | |
| 2005/0267125 A1 | 12/2005 | Luftensteiner et al. | |
| 2006/0030568 A1 | 2/2006 | Zimmerman et al. | |
| 2006/0034927 A1 | 2/2006 | Casadevall et al. | |
| 2006/0142580 A1 | 6/2006 | Loiseleur et al. | |
| 2006/0173182 A1 | 8/2006 | Kankan et al. | |
| 2006/0189635 A1 | 8/2006 | Kramer et al. | |
| 2006/0275372 A1 | 12/2006 | Jenkins et al. | |
| 2007/0036850 A1 | 2/2007 | Rohrich et al. | |

FOREIGN PATENT DOCUMENTS

| | | |
|---|---|---|
| WO | WO 99/03854 | 1/1999 |
| WO | WO 01/47507 | 7/2001 |
| WO | WO 03/090720 | 11/2003 |
| WO | WO 2004/010981 | 2/2004 |
| WO | WO 2004/074502 | 9/2004 |
| WO | WO 2004/106326 | 12/2004 |
| WO | WO 2004/108067 | 12/2004 |

(Continued)

OTHER PUBLICATIONS

Buchdunger et al., "*Inhibition of the Abl protein-tyrosine kinase in vitro and in vivo by a 2- phenylamlnopyrimidine derivative*", Cancer Research, vol. 56, pp. 100-104 (1996).

(Continued)

*Primary Examiner* — Lakshmi Channavajjala
(74) *Attorney, Agent, or Firm* — Kenyon & Kenyon LLP

(57) ABSTRACT

Formulations containing imatinib, preferably imatinib mesylate, with high polymorphic stability and the processes for the preparation thereof are disclosed.

12 Claims, 6 Drawing Sheets a PXRD pattern for imatinib mesylate Form V.

FOREIGN PATENT DOCUMENTS

| WO | WO 2004/108699 | 12/2004 |
| WO | WO 2005/051350 | 6/2005 |
| WO | WO 2005/075454 | 8/2005 |
| WO | WO 2005/077933 | 8/2005 |
| WO | WO 2005/095379 | 10/2005 |
| WO | WO 2006/021458 | 3/2006 |
| WO | WO 2006/024863 | 3/2006 |
| WO | WO 2006/040779 | 4/2006 |
| WO | WO 2006/054314 | 5/2006 |
| WO | WO 2006/121941 | 11/2006 |
| WO | WO 2007/023182 | 3/2007 |
| WO | WO 2007/059963 | 5/2007 |
| WO | WO 2007/119601 | 10/2007 |
| WO | WO 2007/136510 | 11/2007 |

OTHER PUBLICATIONS

Lieberman, H.A. et al. eds., Pharmaceutical Dosage Forms, 1980, at 112, 173.

Nikolova, Z. et al., "*Bioequivalence, safety, and tolerability of imatinib tablets compared with capsules*", 53 Cancer Chemother. Pharmacol. 433, 434 (2004).

Physicians' Desk Reference, 2007 ed., at 2227.

Wade, A. et al. eds, Handbook of Pharmaceutical Excipients 223, 2d ed. 1994.

\* cited by examiner

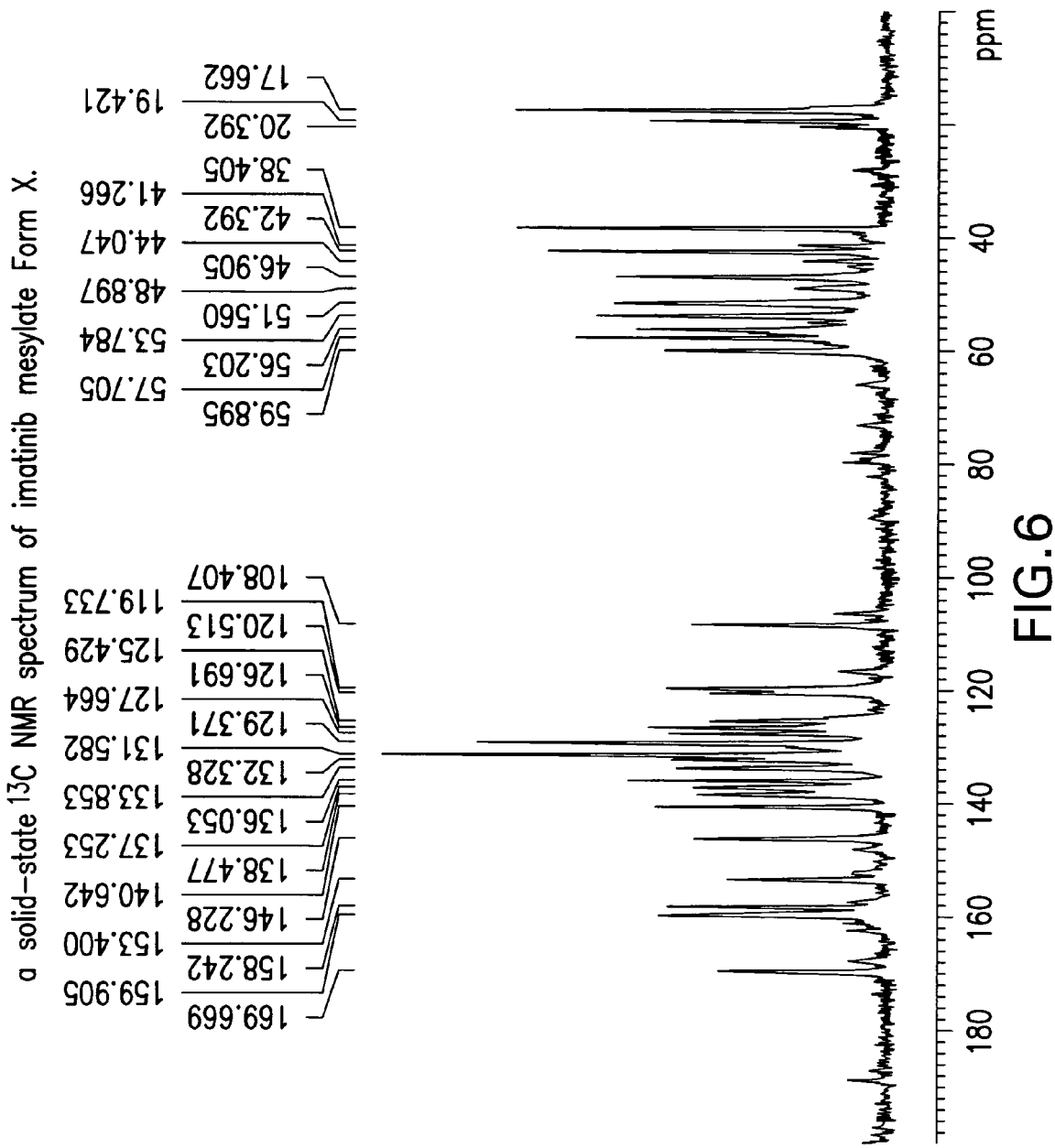

STABLE IMATINIB COMPOSITIONS

CROSS REFERENCE TO RELATED APPLICATIONS

The present invention claims the benefit of the following U.S. Provisional Patent Application Nos. 60/995,321, filed Sep. 25, 2007; and 60/995,651, filed Sep. 26, 2007. The contents of these applications are incorporated herein by reference.

FIELD OF THE INVENTION

The invention relates to formulations containing imatinib with high polymorphic stability.

BACKGROUND OF THE INVENTION

Imatinib mesylate, 4-(4-methylpiperazin-1-ylmethyl)-N-[4-methyl-3-[(4-pyrinin-3-yl)pyrimidin-2-ylamino]phenyl] benzamide mesylate, is a compound having the chemical structure

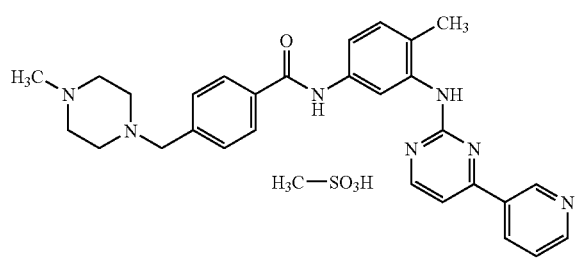

Imatinib is a protein-tyrosine kinase inhibitor. It is especially useful in the treatment of various types of cancer, and can also be used for the treatment of atherosclerosis, thrombosis, restenosis, and fibrosis. Thus imatinib can also be used for the treatment of non-maligant diseases. Imatinib is usually administered orally in the form of a suitable salt, e.g., in the form of imatinib mesylate.

Patent Application Publication Nos. WO 99/03854, WO 2005/077933, WO 2005/095379, WO 2004/106326, WO 2006/054314, WO 2006/024863, WO 2006/048890, US2006/0030568, and WO 2007/023182 and U.S. Pat. No. 6,894,051 purportedly describe amorphous imatinib and crystalline forms of imatinib mesylate designated forms H1, α, α2, β, δ, ε, I, and II.

WO 99/03854, US2006/0030568, and U.S. Pat. No. 6,894,051 purportedly disclose imatinib mesylate forms α and β. Form α is characterized therein by powder X-ray diffraction ("PXRD") pattern having peaks at 4.9, 10.5, 14.9, 16.5, 17.7, 18.1, 18.6, 19.1, 21.3, 21.6, 22.7, 23.2, 23.8, 24.9, 27.4, 28.0, and 28.6±0.2 °2θ. Form β is characterized therein by PXRD pattern having peaks at 9.7, 13.9, 14.7, 17.5, 18.2, 20.0, 20.6, 21.1, 22.1, 22.7, 23.8, 29.8, and 30.8±0.2 °2θ.

WO 2005/077933 purportedly discloses imatinib mesylate crystalline form α2, which is defined herein by a PXRD pattern having peaks at 4.8, 10.4, 11.2, 11.9, 12.9, 13.8, 14.9, 16.4, 17.0, 17.6, 18.1, 18.6, 19.0, 19.8, 21.2, 21.6, 22.6, 23.1, 23.7, 24.9, 26.3, 27.3, 28.5, 31.9, 32.5, and 43.4±0.2 °2θ.

WO 2004/106326 purportedly discloses imatinib mesylate crystalline form H1, which is defined herein by PXRD pattern having peaks at 9.9, 11.1, 16.3, 17.3, 18.1, 19.1, 19.6, 20.3, 21.1, 21.9, 23.2, 23.6, 24.2, 24.9, 25.6, 26.0, 27.3, 27.9, 28.9, 29.4, 30.4, and 30.5±0.2 °2θ. WO 2004/106326 also purportedly discloses amorphous imatinib mesylate hydrate having water content of 2.0-3.2%.

WO 2006/054314 purportedly discloses imatinib mesylate crystalline forms I and II, which are defined herein by PXRD pattern having peaks at 9.7, 10.0, 10.8, 12.5, 13.0, 14.0, 15.2, 16.0, 17.1, 17.9, 18.9, 19.3, 20.0, 20.9, 21.7, 22.4, 23.0, 24.7, 25.2, 25.8, 27.1, 28.0, 28.7, 29.2, 30.2, 30.9, 31.4, 33.3, 36.4, and 38.3±0.2 °2θ, and by peaks at 2.4, 2.8, 4.4, 4.9, 5.5, 7.9, 8.4, 8.9, 9.6, 11.1, 11.5, 12.1, 12.7, 14.1, 14.7, 15.3, 16.1, 17.0, 17.6, 18.6, 19.4, 19.6, 20.3, 20.7, 21.4, 22.0, 22.7, 23.5, 24.0, 24.6, 25.2, 25.7, 26.9, 27.7, 28.2, 28.6, 29.1, 28.5, 30.130.6, 21.8, 33.5, 34.4, 34.9, 35.7, 35.9, 37.1, 37.5, 37.9, 37.2, 39.7, 40.6, 41.3, 43.4, 43.8, 44.6, 45.2, 45.7, 46.5, 47.1, and 48.0±0.2 °2θ, respectively.

WO 2007/023182 purportedly discloses imatinib mesylate crystal forms δ and ε. Form δ is defined herein by PXRD pattern having peaks at 19.2, 19.4, 19.8, 20.3, 20.7, 20.9, and 21.1±0.2 °2θ, and form ε is defined herein by PXRD pattern having peaks at 13.9, 17.0, 17.9, 18.5, 19.6, 20.7, and 24.1±0.2 °2θ. International Patent Application No. WO 2007/136510 describes additional crystalline forms of imatinib mesylate including forms V and X which are described in further detail below.

WO 2003/090720 relates to tablet containing about 30-80% w/w imatinib. Further, WO 01/47507 describes a pharmaceutical composition/tablet containing about 22% w/w imatinib mesylate. Both US 2006/0275372 and WO 2007/119601 describe nanoparticulate compositions of imatinib mesylate.

SUMMARY OF THE INVENTION

In one embodiment, the present invention provides a pharmaceutical composition, preferably a tablet containing imatinib, preferably imatinib mesylate, wherein the pharmaceutical composition provides high polymorphic stability.

In another embodiment, the present invention provides a process for preparing a pharmaceutical composition, preferably a tablet, containing imatinib, preferably imtainib mesylate wherein the pharmaceutical composition provides high polymorphic stability comprising: coating a pharmaceutical composition, preferably a tablet, comprising crystalline imatinib, with a coating solution, preferably a tablet coating solution, containing an organic solvent with an amount of less than about 20% w/v of water, preferably less than 10% w/v, more preferably less than 5% w/v.

BRIEF DESCRIPTION OF THE FIGURES

FIG. 6: a solid-state $^{13}$C NMR spectrum of imatinib mesylate Form X.

DETAILED DESCRIPTION

Figure 1:
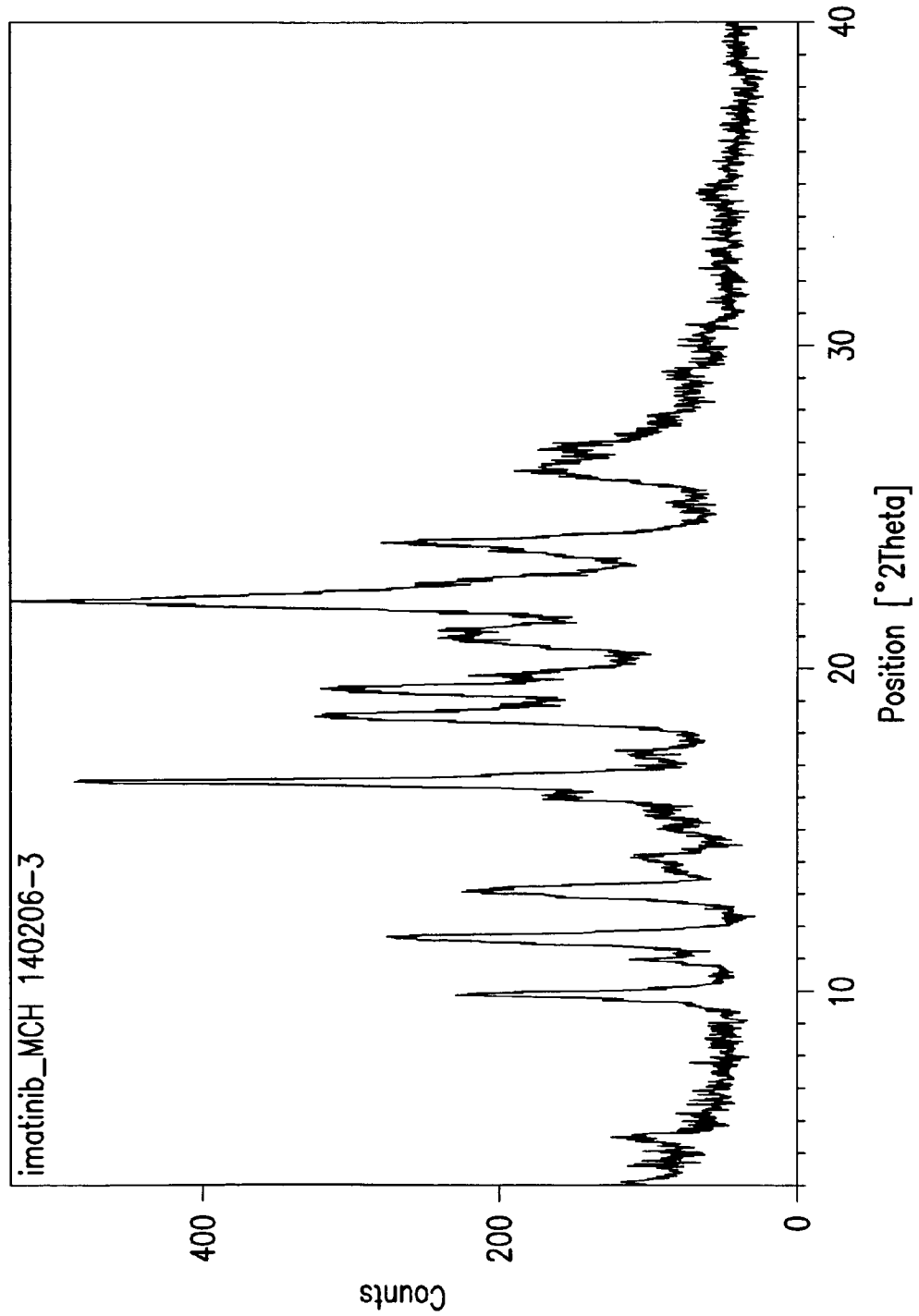
FIG. 1: a PXRD pattern for imatinib mesylate Form V.

The present invention advantageously provides a pharmaceutical composition, preferably a tablet, containing imatinib, preferably imatinib mesylate, wherein the pharmaceutical composition, preferably a tablet formulation, provides polymorphic stability. Preferably, the present invention provides a tablet comprising imatinib mesylate, wherein the tablet provides high polymorphic stability for imatinib mesylate. As used herein term "high stability" refers to not more than 10% conversion, preferably not more than 5% conversion, more preferably not more than 3% conversion of polymorphic form alpha or beta, preferably form beta.

As used herein the term "initial polymorphic form" refers to the polymorphic form of imatinib, preferably imatinib that is formulated in the pharmaceutical composition prior to storage of the pharmaceutical composition. The percentage of initial polymorphic form is at about 100%.

As used herein, the term "polymorphical stability" refers to the stability of imatinib to remain in the original polymorphic form without undergoing polymorphic conversion over time, for example, upon storage.

As used herein, the term "storage" refers to a period of at least about 1 month. Preferably, storage is at 40° C. and 75% RH (relative humidity)

As used herein, the term "polymorphic conversion" refers to the conversion from a polymorphic form to any other polymorphic form of imatinib mesylate, such as conversion into any of forms H1, α, α2, β, δ, ε, I, and II or amorphous form. In embodiments of the present invention the term "polymorphic conversion" refers to the conversion from a polymorphic form V or X of imatinib mesylate to form α or form β, preferably form β.

Polymorphic conversion is measured by techniques known in the art. In particular, each known polymorphic form of imatinib such as forms H1, α, α2, β, δ, ε, I, and II and amorphous form may be characterized by a unique set of PXRD or infrared ("IR") peaks. Using known techniques, the amount of each polymorph in a mixture of polymorphs can be calculated with reference to the relative intensity of the unique characterizing peaks of each polymorph. Preferably, percentage of polymorphic conversion is measured by XRPD, 13-C solid-state NMR or infrared ("IR") peaks. When measured by PXRD, the content of form alpha can be determined by using one or more peaks selected from the following list of peaks 5.0, 10.5, 12.0, 15.0, 18.7, 19.1, 21.4, 28.6±0.2 degrees 2-theta and the content of form beta can be determined by using one or more peaks selected from the following list of peaks 9.7, 13.9, 14.7, 17.5, 18.2, 21.1, 22.1, 22.7, 29.8, 30.8±0.2 degrees 2-theta. The choice of XRPD peaks used for determination can depend on excipients used for formulation. When measured by C-13 solid-state NMR, the content of form alpha is determined by using one or more peaks in the range 100-180 ppm selected from the following list of peaks 112.2, 117.3, 122.3, 126.2, 129.7, 130.1, 134.7, 135.7, 137.9, 142.0, 148.3, 151.5, 158.0, 163.9, 164.7, 165.9±0.2 ppm and content of form beta is determined by using one or more peaks in the range 100-180 ppm selected from the following list of peaks 104.8, 121.5, 123.2, 124.8, 125.9, 128.6, 131.0, 134.9, 136.4, 139.0, 141.7, 146.5, 150.9, 158.9, 168.6±0.2 ppm. The choice of 13C-solid-state NMR shifts used for determination can depend on excipients used for formulation.

The general chapter on "Characterization of crystalline solids by XRPD" of the European Pharmacopoeia 5.08, chapter 2.9.33 may be followed. When measured by XRPD slow scan data collection can be used for suitable detection/quantitation limit or other known procedures. When measured by C-13 solid-state NMR the background can be minimized by long data collection times or other known techniques.

Figure 2:
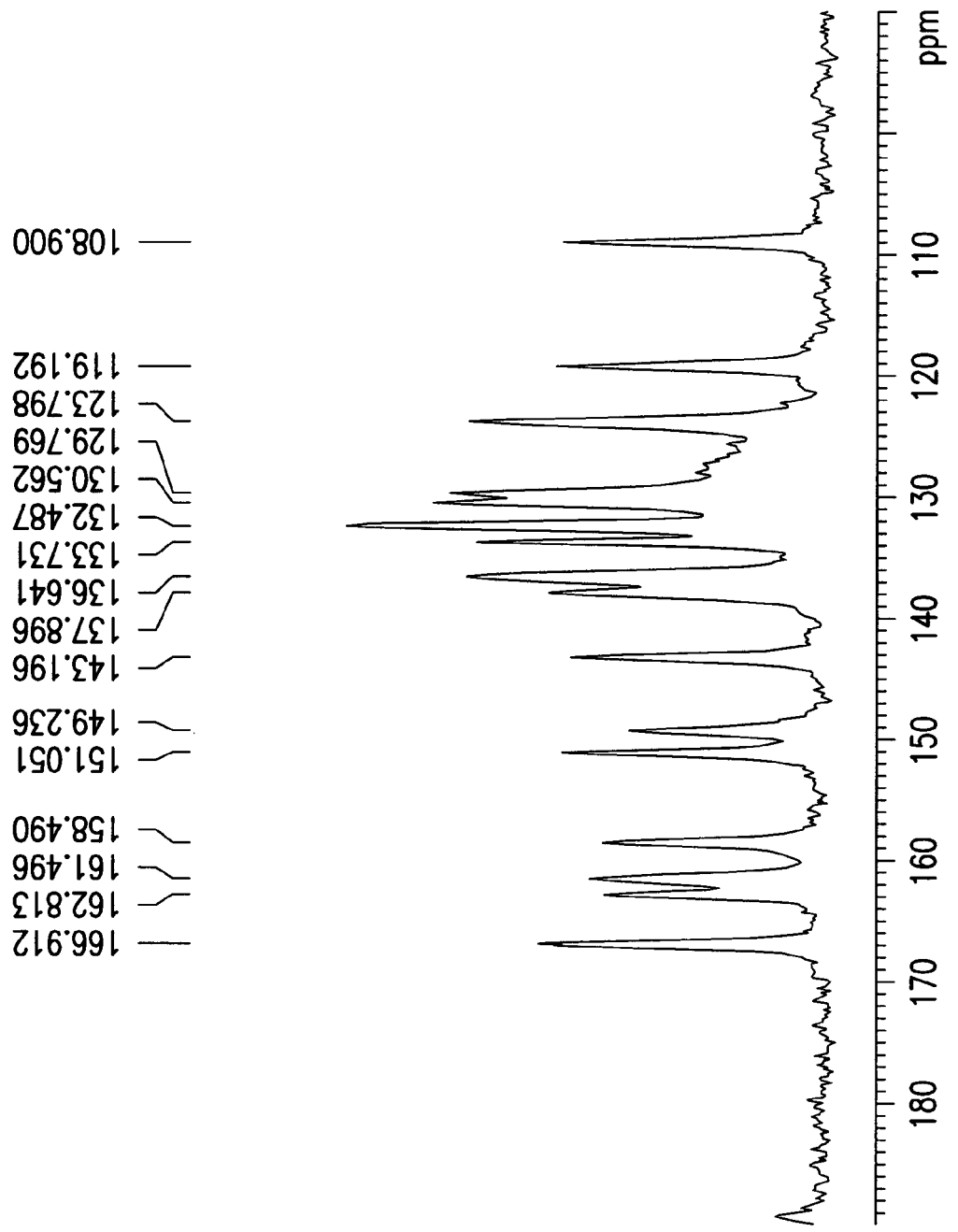
FIG. 2: a solid-state $^{13}$C NMR spectrum of imatinib mesylate Form V in the 100-180 ppm range.
Figure 3:
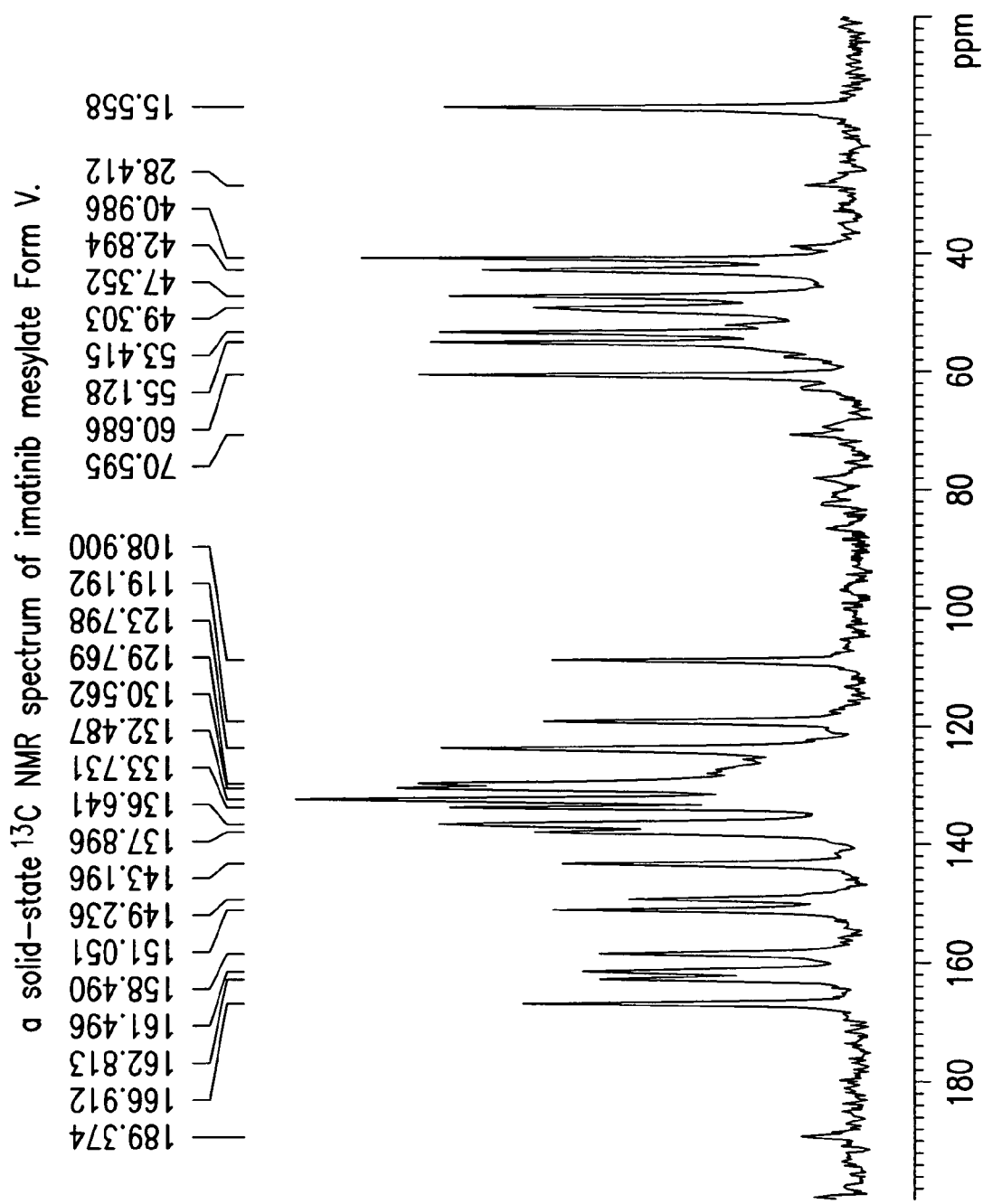
FIG. 3: a solid-state $^{13}$C NMR spectrum of imatinib mesylate Form V.

In a preferred embodiment, the imatinib is in the form of its mesylate salt. More preferably, the imatinib mesylate is in the form of polymorphic form V or form X. Forms V and X are described in detail in co-pending U.S. application Ser. No. 11/796,573, published as US 2008-0090833 (or as internation patent application WO 2007/136510), and which is incorporated herein by reference. Form V is characterized by data selected from the group consisting of: a PXRD pattern with peaks at about 9.9, 11.7, 13.3, 16.6, and 22.1±0.2 °2θ; a PXRD pattern with peaks at about 9.9, 11.7, 13.3, and 16.6±0.2 °2θ; a PXRD pattern with peaks at about: 5.6, 9.9, 11.7, 13.3, 16.6, and 18.5±0.2 °2θ; a PXRD pattern having at least five peaks selected from the list consisting of peaks at about 5.6, 9.9, 11.7, 13.3, 16.6, 18.5, 22.1, 24.0, 26.2, and 26.9±0.2 °2θ; a PXRD pattern depicted in FIG. 1; a solid-state $^{13}$C NMR spectrum with signals at about 162.8, 161.5, and 158.5±0.2 ppm; a solid-state $^{13}$C NMR spectrum having chemical shifts differences between the signal exhibiting the lowest chemical shift and another in the chemical shift range of 100 to 180 ppm of about 53.9, 52.6 and 49.6±0.1 ppm; a solid state $^{13}$C NMR depicted in FIG. 2; and a solid state $^{13}$C NMR spectrum depicted in FIG. 3.

Figure 4:
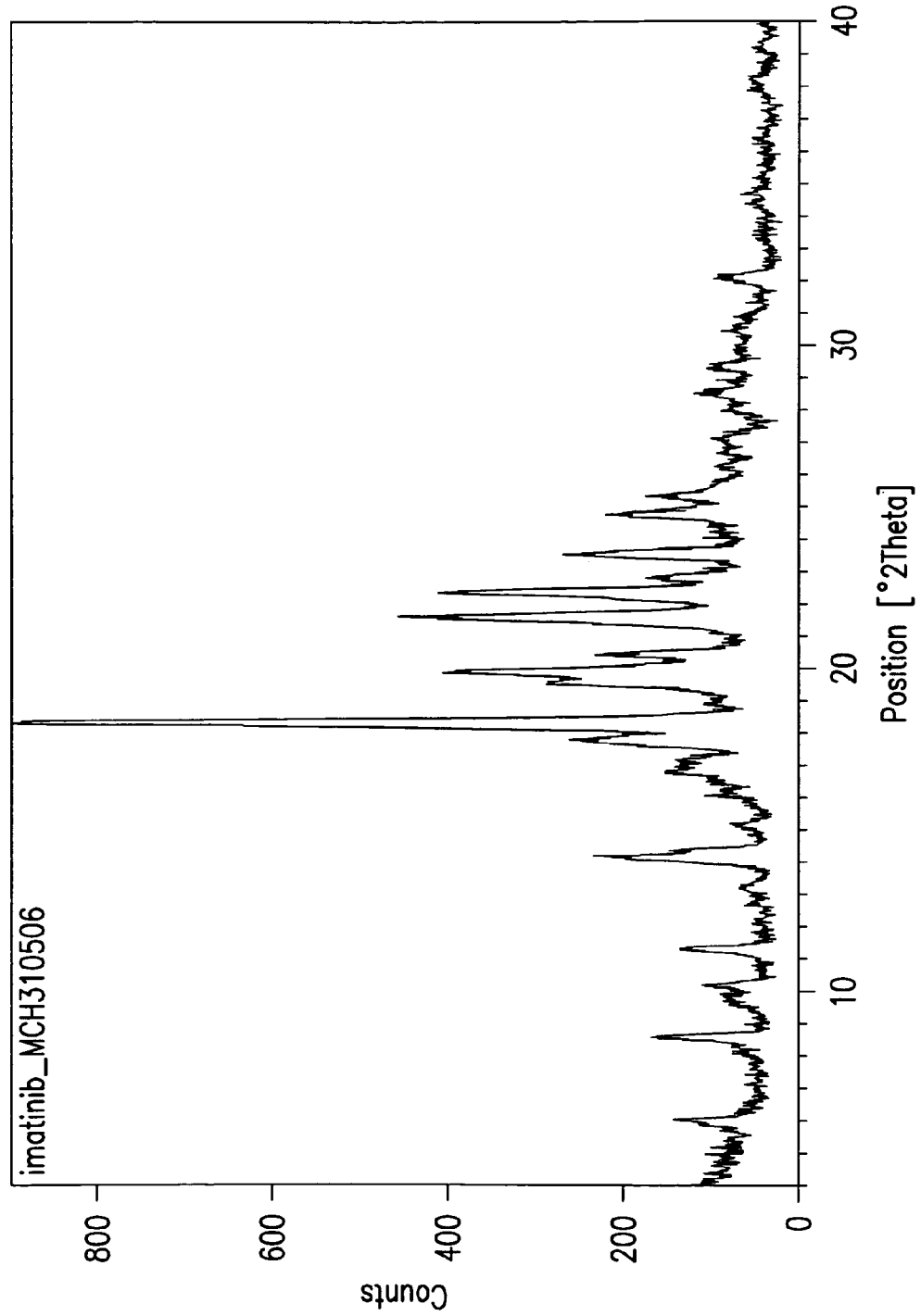
FIG. 4: a PXRD pattern for imatinib mesylate Form X.
Figure 5:
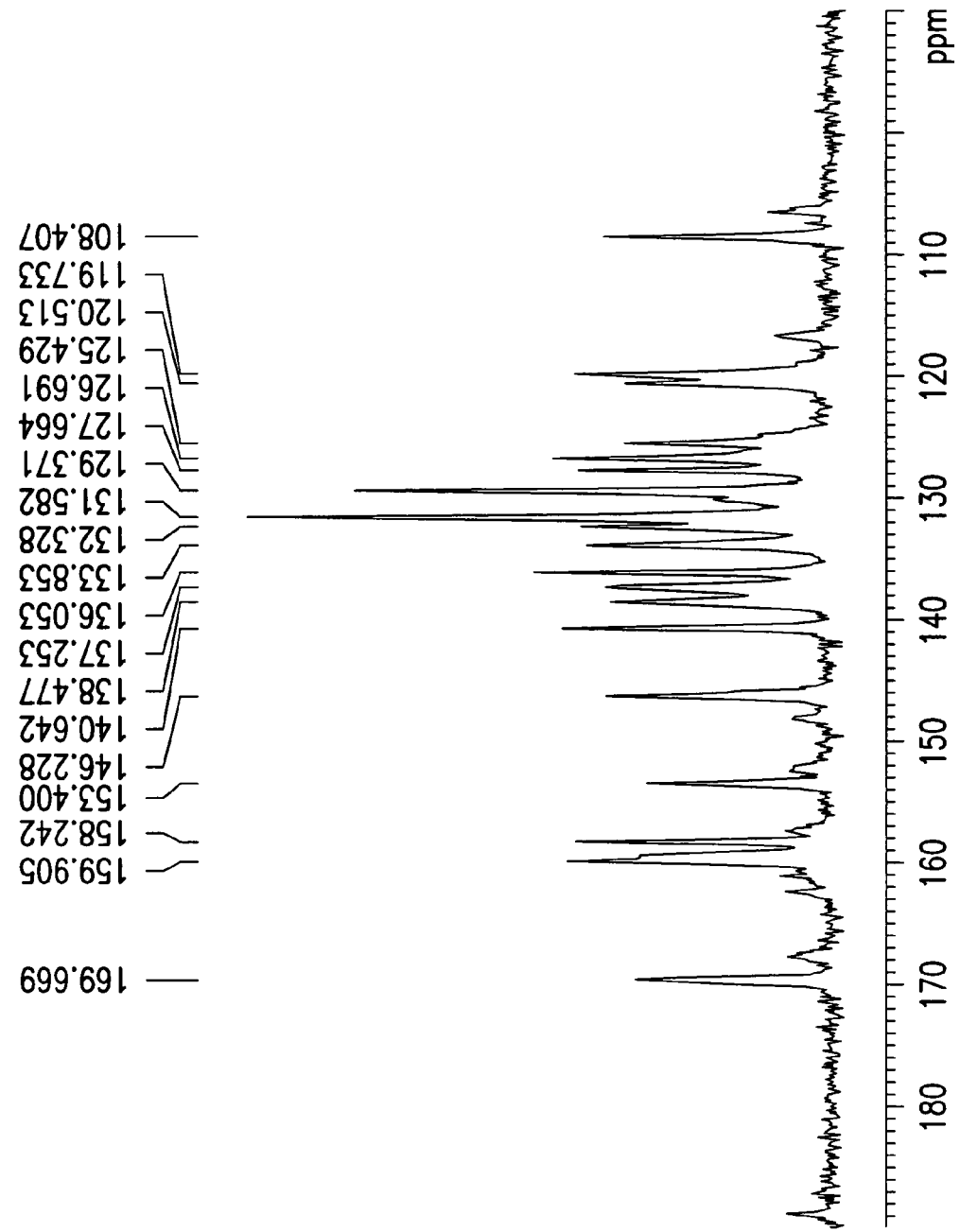
FIG. 5: a solid-state $^{13}$C NMR spectrum of imatinib mesylate Form X in the 100-180 ppm range.

Form X is characterised by data selected from the group consisting of: a PXRD pattern with peaks at about 6.0, 8.6, 11.4, 14.2, 18.3±0.2 °2θ; a PXRD pattern having peaks at about: 6.0, 8.6, 10.2, 11.4, 14.2, ±0.2 °2θ; a PXRD pattern having at least five peaks selected from the list consisting of peaks at about 6.0, 8.6, 10.2, 11.4, 14.2, 17.8, 18.3, 21.6, 22.4, 23.6, and 24.8±0.2 °2θ; a PXRD pattern depicted in FIG. 4; a solid-state $^{13}$C NMR spectrum with signals at about 159.9, 158.2, and 153.4±0.2 ppm; a solid-state $^{13}$C NMR spectrum having chemical shift differences between the signal exhibiting the lowest chemical shift and another in the chemical shift range of 100 to 180 ppm of about 51.5, 49.8, and 45.0±0.1 ppm; a solid-state $^{13}$C NMR spectrum depicted in FIG. 5; and a solid-state $^{13}$C NMR spectrum depicted in FIG. 6.

In one embodiment, the invention encompasses a pharmaceutical composition, preferably a tablet, containing imatinib mesylate Form V or Form X wherein the pharmaceutical composition, preferably tablet, provides polymorphic stability. Preferably, the crystalline imatinib mesylate Form V or Form X do not undergo polymorphic conversion to any of imatinib mesylate forms α or β during preparation or upon storage of the pharmaceutical composition, preferably tablet. More preferably, the crystalline imatinib mesylate does not undergo polymorphic conversion to form β. Further, conversion of the crystalline imatinib mesylate Form V or X in the pharmaceutical composition of the present invention is preferably less than 10%, more preferably less than 5%, and most preferably less than 3% by weight to any other polymorphic form, preferably forms α or β, more preferably form β.

Preferably, the pharmaceutical composition of the present invention comprises a dosage form containing from about 50 mg to about 500 mg, more preferably from about 100 mg to about 400 mg, even more preferably 100 mg or 400 mg imatinib, preferably imatinib mesylate.

The polymorphic stability of the imatinib, preferably imatinib mesylate, in the pharmaceutical composition, preferably tablet, can be attributed to the coating. The coating solution which is applied to the pharmaceutical composition, preferably a tablet, comprising crystalline imatinib mesylate, contains an organic solvent with less then about 20% of water, preferably less than 10%, more preferably less than 5% w/v. Preferably, the solvent is a $C_{1-4}$ alcohol, more preferably ethanol or isopropyl alcohol ("IPA").

Preferably, the uncoated pharmaceutical composition, such as a tablet, of the present invention is prepared by dry granulation or direct compression. Dry granulation may comprise blending a composition containing the active ingredient imatinib, preferably crystalline imatinib mesylate, and one or more excipients; compacting the blend into a slug or a sheet; comminuting the slug or the sheet into compacted granules; and compressing the compacted granules into a tablet.

Direct compression may comprise blending a composition containing the active ingredient imatinib, preferably crystalline imatinib mesylate, and one or more excipients and compressing it directly into a tablet. The compression is directly incorporated into a compacted dosage form using direct compression techniques. Direct compression is easy, simple and applicable for industrial scale. Excipients that are particularly well suited to direct compression tableting include microcrystalline cellulose, spray dried lactose, Starlac (82%-88% Lactose monydrate with 12%-18% Maize starch), dicalcium phosphate dihydrate, and/or colloidal silica. The proper use of these and other excipients in direct compression tabletting is known to those in the art with experience and skill in particular formulation challenges of direct compression tabletting.

The present invention also provides a process for preparing a pharmaceutical composition, preferably a tablet, containing imatinib, preferably imatinib mesylate, wherein the pharmaceutical composition, preferably a tablet, provides polymorphic stability comprising: providing a pharmaceutical composition, preferably a tablet, containing imatinib, preferably imatinib mesylate, which may be prepared according to the above methods, and coating the pharmaceutical composition with a coating solution containing an organic solvent with less then about 20% w/v of water, preferably less than 10% w/v, more preferably less than 5% w/v. Preferably, the solvent is a $C_{1-4}$ alcohol, more preferably ethanol or isopropyl alcohol (IPA). Preferably, the coated pharmaceutical composition is then dried.

Diluents increase the bulk of a solid pharmaceutical composition and can make a pharmaceutical dosage form containing the composition easier for the patient and caregiver to handle. Diluents for solid compositions include, for example, microcrystalline cellulose (e.g. AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. EUDRAGIT®), potassium chloride, powdered cellulose, sodium chloride, sorbitol and talc. Most preferably, the diluent is lactose.

Solid pharmaceutical compositions that are compacted into a dosage form like a tablet can include excipients whose functions include helping to bind the active ingredient and other excipients together after compression. Binders for solid pharmaceutical compositions include at least one of acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®, pregelatinized starch, sodium alginate, or starch.

The dissolution rate of a compacted solid pharmaceutical composition in the patient's stomach can be increased by the addition of a disintegrant to the composition. Disintegrants include, but are not limited to, alginic acid, carboxymethylcellulose calcium, carboxymethylcellulose sodium (e.g. AC-DI-SOL @PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) or starch. Most preferably the disintegrants are selected from the group consisting of: crospovidone, microcrystalline cellulose and mixtures thereof.

Glidants can be added to improve the flow properties of non-compacted solid composition and improve the accuracy of dosing. Excipients that can function as glidants include colloidal silicon dioxide, magnesium trisilicate, powdered cellulose, starch, talc, and/or tribasic calcium phosphate. Most preferably the glidant is colloidal silicon dioxide.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and/or zinc stearate. Most preferably the lubricant is magnesium stearate.

Flavoring agents and flavor enhancers make the dosage form more palatable to the patient. Common flavoring agents and flavor enhancers for pharmaceutical products that can be included in the composition of the present invention include, but are not limited to, maltol, vanillin, ethyl vanillin, menthol, citric acid, fumaric acid, ethyl maltol, or tartaric acid. Solid compositions can also be dyed using any pharmaceutically acceptable colorant to improve their appearance and/or facilitate patient identification of the product and unit dosage level.

Selection of excipients and the amounts to use can be readily determined by the formulation scientist based upon experience and consideration of standard procedures and reference works in the field.

In a preferred embodiment tablets in accordance with the present invention comprise: From 20 to 80% w/w imatinib mesylate; from 10 to 60% w/w, more preferably from about 25% to about 60% w/w of a diluent, filler or bulking agent, preferably lactose, more preferably starlac (82-88% Lactose monohydrate and 12-18% Maize starch); from 4 to 30% w/w, more preferably from about 10% to about 25% w/w, of a disintegrant, preferably crospovidone; from about 0 to about 10% w/w, more preferably from about 1.5 to 9% w/w of a another disintegrant, preferably microcrystalline cellulose; from about 0 to about 5% w/w, more preferably 1 to 5% w/w of another binder, preferably hydroxy propyl cellulose (KLUCEL®); from 0.2 to 5% w/w of a glidant, preferably colloidal silicon dioxide, mannitol or aerosil, or a combination thereof; and from 0.1 to 4% w/w, more preferably from about 0.5% to about 2% w/w, of a lubricant, preferably magnesium stearate or sodium stearyl fumarate.

More preferably, each tablet contains;
- 119.5 mg imatinib mesylate;
- 117.3 mg lactose;
- 0-18.0 mg crospovidone;
- 48.0 mg microcrystalline cellulose;
- 18.0 mg Klucel;
- 68.0 mg Mannitol;
- 2.5 mg Aerosil and;
- 12.7 mg sodium stearyl fumarate; and
- 9.0 mg Opadry (coating).

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

The following examples are given for the purpose of illustrating the invention and shall not be construed as limiting the scope or spirit of the invention.

EXAMPLES

Instruments
Powder X-ray Diffraction

XRD diffraction was performed on X-Ray powder diffractometer: PanAlytical X'pert Pro powder diffractometer, Cu-tube, scanning parameters: CuKα radiation, λ=1.5418 Å. Continuous scan at a rate of: 0.02 °2theta/0.3 sec.

13C NMR

The CP/MAS 13C NMR measurements were made at Bruker Avance 500 NMR US/WB spectrometer in 4-mm ZrO2 rotor. Magic angle spinning (MAS) speed was 10 kHz. As used herein, the term "13C NMR chemical shifts" refers to the shifts measured under above specified conditions, however, these shifts can slightly differ instrument to instrument and can be shifted either upfield or downfield due to the different instrumental setup and calibration used. Nevertheless the sequence of individual peaks remains identical.

Example 1

Tablets with Coated with Ethanol

Imatinib Mesylate 100 mg Tablets:

| mg per core | Raw Materials | Sign. Prod. Dept. | 5,000 Cores kg | g |
|---|---|---|---|---|
| | PART I | | | |
| 119.5 | Imatinib Mesylate | | 597 | 500 |
| 117.3 | Lactose MNHDR (DCL-14) | | 586 | 500 |
| 48.0 | Avicel PH 200 | | 240 | 000 |
| 34.0 | Mannitol SD 200 | | 170 | 000 |
| 18.0 | Klucel | | 90 | 000 |
| | Part II | | | |
| 34.0 | Manitol SD 200 | | 170 | 000 |
| 2.5 | Aerosil 200 | | 12 | 500 |
| | Part III | | | |
| 12.7 | Sodium Stearyl Fumarate | | 63 | 500 |
| 386 | Theoretical End Weight | 1 | 930 | 000 |

The coating of the above formulation:

| mg per core | Excess 80% | Raw Materials | 500 TABLETS kg | g | mg |
|---|---|---|---|---|---|
| 386.0 | | Imatinib Mesylate 100 mg | | 193 | 000 |
| 9.0 | | Opadry 21S32726 Yellow Ethanol 95% | | | |
| 395.0 | | Theoretical Weight of Tablets | | | |

Example 2

Tablets with Coated with H₂O (Comparative Example)

Imatinib Mesylate 100 mg Tablets

| mg per core | Raw Materials | Sign. Prod. Dept. | 5,000 Cores kg | g |
|---|---|---|---|---|
| | PART I | | | |
| 119.5 | Imatinib Mesylate | | 597 | 500 |
| 117.3 | Lactose MNHDR (DCL-14) | | 586 | 500 |
| 48.0 | Avicel PH 200 | | 240 | 000 |
| 34.0 | Mannitol SD 200 | | 170 | 000 |
| 18.0 | Klucel | | 90 | 000 |
| | Part II | | | |
| 34.0 | Mannitol SD 200 | | 170 | 000 |
| 2.5 | Aerosil 200 | | 12 | 500 |
| | Part III | | | |
| 12.7 | Sodium Stearyl Fumarate | | 63 | 500 |
| 386 | Theoretical End Weight | 1 | 930 | 000 |

Aqueous coating to the above formulation

| mg per core | Excess 80% | Raw Materials | 500 TABLETS kg | g | mg |
|---|---|---|---|---|---|
| 386.0 | | Imatinib Mesylate 100 mg | | 193 | 000 |
| 9.0 | | Opadry II OY-GM 28900 white Purified water | | | |
| 395.0 | | Theoretical Weight of Tablets | | | |

* Solids remaining on tablet

Example 3

Comparison in Polymorphic Stability after Storage at 40° C. and 75% Relative Humidity (RH).

Tablets prepared and coated according to the above formulations were stored for various amounts of time at 40° C. and 75% RH. As indicated in the table below some tablets are coated with a coating using 95% ethanol and others were coated using water as in example 2 above. The imatinib used was crystalline imatinib mesylate form X. The results show that in tablets coated with a tablet coating using ethanol the polymorphic form of imatinib is retained over time whereas when water is used in tablet coating the tablet form X of imatinib is converted to form Beta of imatinib in the formulation.

| Stability at 40° C. and 75% Relative Humidity | | | |
|---|---|---|---|
| | Time | XRD | |
| Sample | Interval | Result | Comment |
| EtOH Coating Form X | t = 0 | Form X | |
| Water Coating Form X | t = 0 | Form X | |

Stability at 40° C. and 75% Relative Humidity

| Sample | Time Interval | XRD Result | Comment |
|---|---|---|---|
| EtOH Coating | 1 Month | Form X | Diffraction at 18.8° 2 theta increase probably change in crystallinity. |
| Water Coating | 1 Month | Form Beta | more than 90% |
| Water Coating | 2 Months | Form Beta | more than 90% |

What is claimed:

1. A pharmaceutical composition in the form of a coated tablet comprising polymorphic form X of imatinib mesylate, wherein less than 10% of the polymorphic form of imatinib mesylate is converted to form α or form β after storage at 40° C. at 75% relative humidity for 1 month, and wherein the coated tablet is prepared by coating a tablet using a $C_{1-4}$ alcohol solvent with less than 20% w/v water.

2. The pharmaceutical composition of claim 1, wherein less than 5% of the polymorphic form X of imatinib mesylate is converted.

3. The pharmaceutical composition of claim 2, wherein less than 3% of the polymorphic form X of imatinib is converted.

4. The pharmaceutical composition of claim 1, wherein less than 10% of the imatinib mesylate form X is converted to imatinib mesylate form β.

5. The pharmaceutical composition of claim 1, wherein the coated tablet is prepared by coating a tablet using a $C_{1-4}$ alcohol solvent with less than 10% w/v water.

6. The pharmaceutical composition of claim 1, wherein the $C_{1-4}$ alcohol is ethanol or isopropyl alcohol.

7. The pharmaceutical composition of claim 1, comprising from about 20 to about 80% w/w imatinib mesylate; from about 10 to about 60% w/w of a diluent; from about 4 to about 30% w/w of a disintegrant; from about 0 to about 9% w/w of another disintegrant; from about 0 to about 5% w/w of a binder; from about 0.2 to about 5% w/w of a glidant; from about 0.1 to about 4% w/w of a lubricant, and from about 1.5% to about 3% w/w of a coating.

8. The pharmaceutical composition of claim 7, wherein the diluent is lactose, the disintegrant is crospovidone or microcrystalline cellulose, the binder is hydroxypropyl cellulose, the glidant is colloidal silicon dioxide, and the lubricant is magnesium stearate or sodium stearyl fumarate.

9. A process of preparing the pharmaceutical composition according to claim 1, said process comprising:
providing a tablet comprising crystalline form X of imatinib mesylate, and coating the tablet with a tablet coating using a $C_{1-4}$ alcohol solvent with less than 10% w/v of water.

10. The process of claim 9, wherein the tablet is provided by preparing a tablet comprising a method selected from dry granulation and direct compression of a mixture comprising imatinib mesylate.

11. The process of claim 10, wherein the tablet is prepared comprising mixing imatinib mesylate, a diluent, one or more disintegrants, and a binder; adding glidant to the obtained mixture;
and adding a lubricant to the so obtained mixture to obtain a final blend to form a dosage form.

12. The process of claim 9, wherein the $C_{1-4}$ alcohol is ethanol or isopropyl alcohol.

* * * * *